United States Patent [19]

Bigelow et al.

[11] 3,932,451

[45] Jan. 13, 1976

[54] 1,4,7,10-TETRAAZATETRACYCLO[5.5.1.0$^{4,13}$.0$^{10,13}$]TRIDECANE AND ITS CONJUGATE ACIDS

[75] Inventors: John Howard Bigelow, Rochester, N.Y.; Jack E. Richman, Wilmington, Del.

[73] Assignee: E. I. Du Pont de Nemours & Company, Wilmington, Del.

[22] Filed: Nov. 27, 1973

[21] Appl. No.: 419,441

[52] U.S. Cl. ............... 260/309.6; 99/66.5; 99/107; 260/239 B; 260/309.7; 260/482 C
[51] Int. Cl.$^2$ .......................................... C07D 49/34
[58] Field of Search ...................... 260/309.7, 309.6

[56] References Cited
OTHER PUBLICATIONS
Chem. Abstracts, 65: 18580c.

Primary Examiner—Ethel G. Love
Attorney, Agent, or Firm—Anthony P. Mentis

[57] ABSTRACT

1,4,7,10-Tetraazatetracyclo[5.5.1.0$^{4,13}$.0$^{10,13}$]tridecane -tridecane which can reversibly and successively add two moles of acids to form conjugate acids, can be made by condensation of 1,4,7,10-tetraazacyclododecane with ethyl orthocarbonate or by the condensation of 2,3,5,6-tetrahydro-1H-imidazo[1,2-a]imidazole with ethyl bis(2-chloroethyl)carbamate followed by acid hydrolysis. The salts with acids having photographically innocuous anions can be used in developers for silver halide emulsion to reduce fog, and can be used in the emulsions themselves as sensitizers.

5 Claims, No Drawings

1,4,7,10-TETRAAZATETRACYCLO[5.5.1.0⁴,¹³.0¹⁰,¹³]TRIDECANE AND ITS CONJUGATE ACIDS

FIELD OF THE INVENTION

This invention relates to a novel tetracyclic tetraamine and its tricyclic salts made by reaction of the tetraamine with acids having photographically innocuous anions.

DESCRIPTION OF THE INVENTION

This invention is directed to the tetraamine 1,4,7,10-tetraazatetracyclo[5.5.1.0⁴,¹³.0¹⁰,¹³]tridecane (formula I), to its salts with one or two equivalents of an acid having a photographically innocuous anion, to developer for silver halide emulsions containing an amount of the tetraamine or its salts sufficient to reduce background fog, and to the use of such compounds in photographic silver halide emulsions in an amount sufficient to sensitize said emulsion.

The tetraamine of this invention and its equilibrium with the salts 1,2,3,4,6,7,8,9-octahydro-5H-4a-azonia-2a,7,9a-triazacycloocta[cd]pentalene chloride (formula II) and 1,2,3,4,6,7,8,9-octahydro-5H-4a-azonia-2a,7,9a-triazacycloocta[cd]pentalene chloride hydrochloride (formula III) in the presence of hydrochloric acid, which are preferred salts is shown in the following equation:

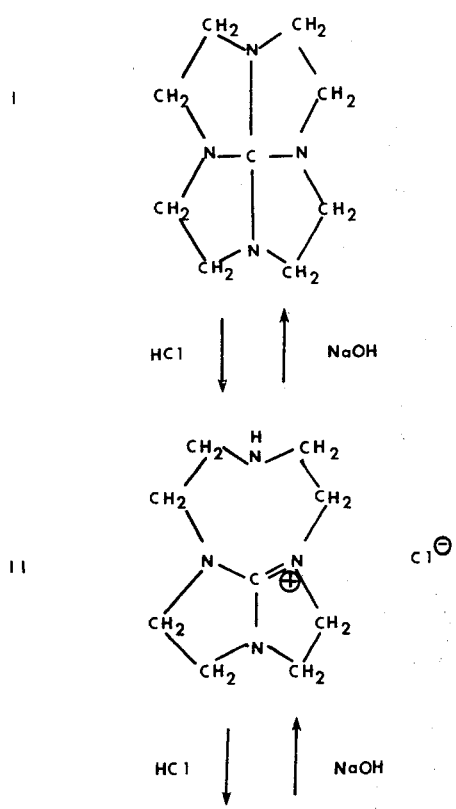

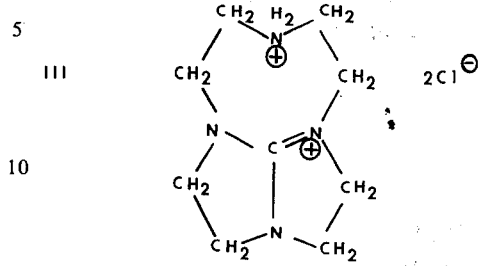

The interconversions depicted in the preceding equation all take place rapidly at room temperature. Treatment of I with one equivalent of hydrochloric acid produces II; treatment of II with one equivalent of a strong base such as aqueous sodium hydroxide reconverts II to I. Treatment of II with one or more equivalents of hydrochloric acid produces III; treatment of III with one equivalent of a strong base such as aqueous sodium hydroxide converts it to II. I and III can be interconverted directly without stopping at II; i.e., by treating I with two or more equivalents of hydrochloric acid and by treating III with two or more equivalents of sodium hydroxide.

The organic, cationic moieties of II and III are the monoprotonated and diprotonated conjugate acids of I, respectively. Correspondingly, I is the conjugate base formed by removing one proton from the cation of II or two protons from the cation of III. The facile equilibrium between the base I and the conjugate acids II and III is unusual, in that a C-N bond is broken and reformed in the processes. Usually there is no such bond rupture in the interconversions of conjugate acids and bases.

In II the unit positive charge assigned to one of the ring nitrogen atoms is actually shared by the three nitrogens bonded to the central carbon, and to a lesser extent by the central carbon, to give a resonance-stabilized structure. The structure shown for II is one of several localized structures contributing to the overall structure. It is used both for convenience and to make it easier to name the compound. The same is true for the corresponding unit positive charge in III.

The tetraamine of the invention and its chloride salts can be prepared as shown in the following examples. Of the starting materials used in Example A, 2,3,5,6-tetrahydro-1H-imidazo[1,2-a]imidazole was prepared essentially by the method of McKay et al., J. Am. Chem. Soc. 78, 6144 (1956), and was purified by recrystallization from acetonitrile; ethyl bis(2-chloroethyl)carbamate was prepared by the method of Skipper et al., J. Nat. Cancer Inst. 9, 77 (1948).

Salts of other acids such as sulfuric acid, nitric acid, acetic acid, tartaric acid and lactic acid having photographically innocuous anions can be made by conventional metathetic reactions.

The term "photographically innocuous anion" is intended to mean an anion whose presence in a photographic silver halide emulsion and/or in a developer solution therefor, has little or no effect on the photographic process.

This invention is further illustrated by the following examples which are not intended to be limiting.

EXAMPLE A

7-Ethoxycarbonyl-1,2,3,4,6,7,8,9-octahydro-5H-4a-azonia-2a,7,9a-triazacycloocta[cd]pentalene tetraphenylborate

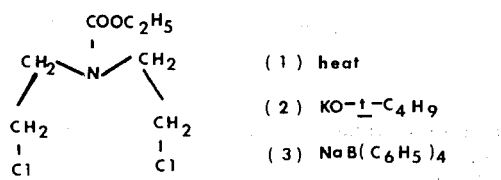

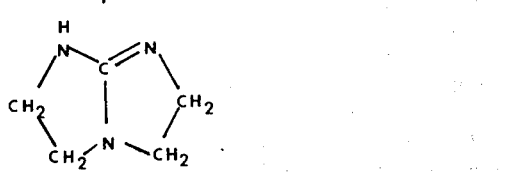

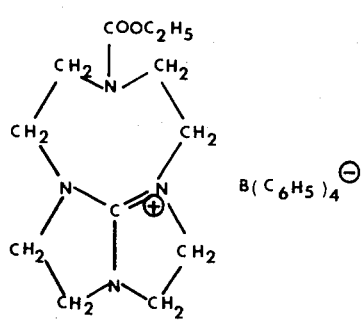

To a stirred solution of 3.11 g of ethyl bis(2-chloroethyl)carbamate in 30 ml of dry dimethylformamide was added 1.62 g of 2,3,5,6-tetrahydro-1H-imidazo[1,2-a]imidazole. The mixture was warmed until it became homogeneous (ca. 40°–50°C). On cooling, the starting imidazole crystallized, and the reaction mixture remained strongly basic. The mixture was still strongly basic after stirring at 70°–80°C for 5 minutes and after stirring at 100°C for 15 minutes. It was heated at about 100°C on a steam bath for 2.5 hours, after which titration of a 1.0-ml sample with 0.1 N HCl showed that 65% of the original base had been neutralized. Heating on the steam bath was continued for 1.75 hours, followed by stirring at ambient temperature overnight, after which the mixture was only weakly basic to phenolphthalein. The absence of basicity indicated that the first stage of the desired reaction, i.e., reaction of one of the 2-chloroethyl groups at the NH group of the imidazole with elimination of HCl, was essentially complete. The results also indicated that heating the reaction mixture for one 6-hour period at 100°C would suffice for this part of the process.

There was then added to the mixture 16.8 ml of 0.86 M potassium t-butoxide in dimethylformamide, and the resulting slurry was heated at 100°C with stirring for about 20 hours. The solution was concentrated under reduced pressure to give 4.4 g of an oil, of which 3.5 g was dissolved in water and treated with excess aqueous sodium tetraphenylborate. The white solid that precipitated was separated by filtration, washed with ethyl alcohol, and recrystallized from acetonitrile, to give 2.17 g of 7-ethoxycarbonyl-1,2,3,4,6,7,8,9-octahydro-5H-4a-azonia-2a,7,9a-triazacycloocta[cd]pentalene tetraphenylborate. A smaller sample of the product, similarly prepared from the nonvolatile oil and recrystallized from acetonitrile, melted at 201.5°–203°C.

Anal. Calcd. for $C_{36}H_{41}BN_4O_2$: C, 75.52; H, 7.22; N, 9.79
Found: C, 75.13; H, 7.35; N, 9.85
74.86  7.24  9.89

NMR (220 MHz, $CD_3CN$): $\delta$ 7.25 (m, 8H, meta), 6.99 (t, 8H, ortho), 6.82 (t, 4H, para), 4.11 (quartet, 2H, C$\underline{H}_2$,CH$_3$), 3.93, 3.66, 3.51 and 3.33 (all triplets, 4H each) and 1.26 (t, 3H, C$\underline{H}_3$).

A second recrystallization of this sample from acetonitrile gave mp 201°–202°C and the following analytical data:

Found: C, 75.34; H, 7.46; N, 9.88
75.04  7.42  9.61

EXAMPLE 1

1,2,3,4,6,7,8,9-Octahydro-5H-4a-azonia-2,7,9a-triazacycloocta[cd]pentalene chloride hydrochloride

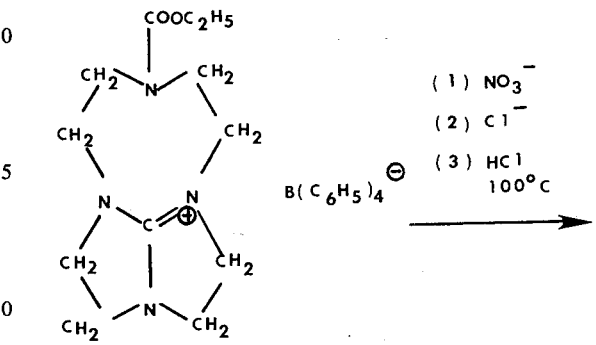

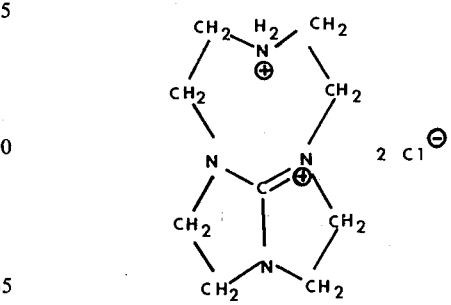

a. The tetraphenylborate salt that was the product of Example A (2.0 g) was converted to the corresponding nitrate by dissolving it in 40 ml of warm acetonitrile and adding a solution of 0.60 g of silver nitrate in 10 ml of acetonitrile. After 30 minutes the precipitated silver tetraphenylborate was separated by filtration, and the filtrate was evaporated to give 1.12 g of crystalline nitrate. This was converted to the corresponding chloride by dissolving it in water and passing the solution through an anion-exchange column containing quaternary ammonium chloride residues on crosslinked polystyrene ("Dowex" 2-X8). An aqueous solution of the chloride in 20 ml of water was thus obtained. The identity of the product was confirmed by evaporating one-fifth of this solution to give 199 mg of the chloride and observing the similarity of the aliphatic region of its nmr spectrum in $D_2O$ with the spectrum of the tetraphenylborate used as starting material.

Another one-fifth of the aqueous solution was saturated with hydrogen chloride at 25°C, and the resulting solution was heated in a sealed glass tube at 100°C for 60 hours. The resulting solution was concentrated under vacuum to give 110 mg of solid 1,2,3,4,6,7,8,9-octahydro-5H-4a-azonia-2a,7,9a-triazacycloocta[cd]pentalene chloride hydrochloride.

b. A larger sample of the product, prepared by the same method and washed with isopropyl alcohol, melted at 149°–154°C. Recrystallization from absolute ethyl alcohol gave colorless crystals, mp 151°–153°C. These crystals were apparently a solvate, since on drying at about 80°C in vacuum they became opaque and had mp 250°–252°C. The following analyses were carried out on the vacuum-dried sample.

Anal. Calcd. for $C_9H_{18}Cl_2N_4$: C, 42.69; H, 7.17; N, 22.13 Found: C, 42.17; H, 6.83; N, 22.38.

IR(KBr, solvent-free): 2.92 (strong), 3.38, 3.45, 3.6–3.77 (several broad bands), 3.91, 4.20, 4.65 (weak), 5.95 (strong), 6.10 (weak), 6.24 (strong), 6.72, 6.83, 7.21, 7.27, 7.54, 7.74 (strong), 8.31, 8.71, 9.02, 9.18, 9.51, 10.05, 10.21, 10.45, 10.56, 11.7–12.2, 13.10, 14.25 (shoulder) and 14.50$\mu$ (broad).

NMR ($D_2O$): 27-line pattern composed of 2 overlapping symmetrical AA'BB' patterns with approximate shifts of (4.23 and 3.57 ppm) and (3.93 and 3.67 ppm).

When excess aqueous sodium picrate solution was added to an aqueous solution of a small amount of the product in a, a yellow dipicrate precipitated, mp 245°–250°C (dec). In this compound the two chloride ions of the product of the example have been replaced by picrate ions. Another sample of the dipicrate, similarly prepared, was recrystallized from acetonitrile; mp 255°–259°C (dec).
An infrared absorption spectrum of the picrate was also obtained.

EXAMPLE 2

1,4,7,10-Tetraazatetracyclo[5.5.1.0$^{4,13}$.0$^{10,13}$]tridecane

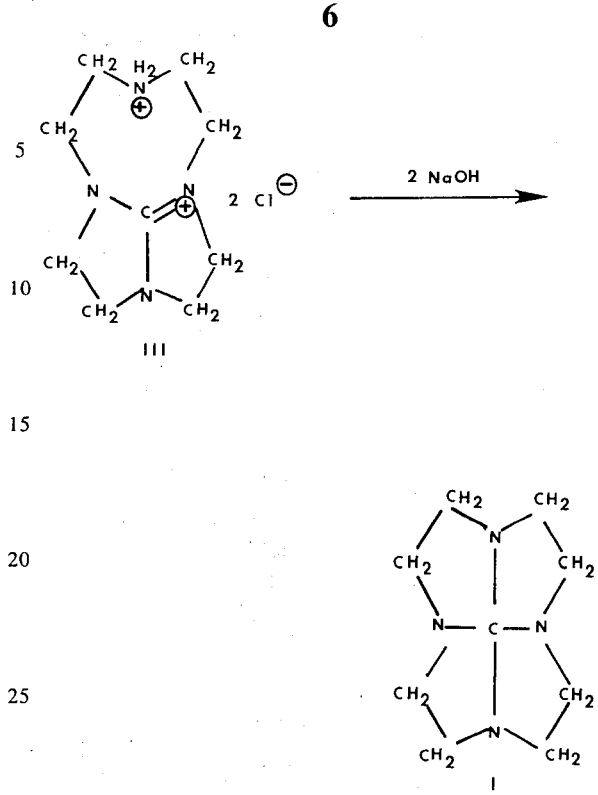

To a solution of 110 mg of 1,2,3,4,6,7,8,9-octahydro-5H-4a-azonia-2a,7,9a-triazacycloocta[cd]pentalene chloride hydrochloride in 0.5 ml of $D_2O$ was added 0.3 g of a 14% (by weight) solution of sodium hydroxide in $D_2O$ and then 0.4 ml of chloroform-d. The mixture was shaken thoroughly, and the organic phase was allowed to settle out. The nmr absorption spectrum of the organic phase showed a single symmetrical $A_2B_2$ pattern shifted to higher fields than the complex pattern of the starting material. Evaporation of the organic phase gave 1,4,7,10-tetraazacyclo[5.5.1.0$^{4,13}$.0$^{10,13}$]tridecane as a white solid. When an aqueous solution of the product was acidified with excess aqueous picric acid, a yellow solid precipitated. The latter product had an infrared absorption spectrum identical with that of the dipicrate described in Example 1. It melted at 240°–245°C (dec).

EXAMPLE 3

1,4,7,10-Tetraazatetracyclo[5.5.1.0$^{4,13}$.0$^{10,13}$]tridecane a. A solution of 6.7 g of 1,2,3,4,6,7,8,9-octahydro-5H-4a-azonia-2a,7,9a-triazacycloocta[cd]pentalene chloride hydrochloride in 50 ml of water was prepared by scaling up the method of Example 1. Enough sodium Anal. Calcd. for $C_{21}H_{22}N_{10}O_{14}$: C, 39.50, H, 3.47; N, 21.94
Found: C, 40.14; H, 3.49; N, 21.78
39.96           3.49        21.72 hydroxide was dissolved in 40 ml of this solution to make it strongly basic. The resulting solution was extracted with several portions of chloroform, and the combined extracts were dried over 3A molecular sieves for 50 minutes. The infrared absorption spectrum of the chloroform solution indicated that water of hydration was still present after this treatment. The chloroform was removed by distillation under nitrogen. The residue was heated in a bulb-to-bulb distillation apparatus at 70°–110°C (oven temperature) and 2 mm and then at 110°–150°C at 9 mm. A total of 2.55 g of 1,4,7,10-tetraazatetracyclo[5.5.1.0$^{4,13}$.0$^{10,13}$]tridecane volatilized as a solid sublimate and a semisolid distillate. The distillate soon became entirely solid. A sample of the sublimate melted at 97°–104.5°C and gave the following analyses:

NMR (CCl$_4$): Symmetrical AA'BB' pattern, 14 lines centered at δ2.83.

NMR (CD$_3$CN): Broad singlet (width at half height ~8 Hz) at δ2.83 at 35°C splitting to a broadened symmetrical multiplet at −30°C.

Mass Spectrum: m/e (rel. intensity) 180 (100, parent peak), 179 (10), 152 (30–40), 138 (15–20), 124 (80–90), 110 (15–20), 98 (40–50), 56 (20–30), 55 (15–20) and 42 (20–25).

Titration with hydrochloric acid gave two end points by glass-electrode potentiometry, corresponding to an equivalent weight of 91 ± 9 and a molecular weight of 182 ± 18 for a dibasic amine. The calculated values for C$_9$H$_{16}$N$_4$ are 90 and 180, respectively.

b. 1,4,7,10-Tetraazatetracyclo[5.5.1.0$^{4,13}$.0$^{10,13}$]tridecane was prepared essentially by the method described above and was distilled in a bulb-to-bulb apparatus at about 140°C/7 mm. The colorless solid melted at 105°–108°C. Analysis indicated that the product was a hydrate containing an average of 0.73 molecule of water per molecule of tetraamine.

| Anal. Calcd. for C$_9$H$_{16}$N$_4$·0.73 H$_2$O: | | | |
|---|---|---|---|
| | C, 55.88; | H, 9.10; | N, 28.97 |
| Found: | C, 56.00; | H, 8.86; | N, 29.03 |
| | 55.70 | 8.96 | 29.32 |

Acidification of an aqueous solution of the product with excess aqueous picric acid caused a yellow dipicrate to precipitate. The latter was recrystallized three times from aqueous acetonitrile, after which it melted at 255°–259°C (dec) and was shown to be identical with the picrates described in Examples 1 and 2 by comparison of the infrared absorption spectra.

| Anal. Calcd. for C$_{21}$H$_{22}$N$_{10}$O$_{14}$: | C, 39.50; | H, 3.47; | N, 21.94 |
|---|---|---|---|
| Found: | C, 39.52; | H, 3.17; | N, 21.60 |
| | 39.97 | 3.28 | 21.85 |
| | 39.56 | 3.17 | 21.65 |

IR (KBr): 2.9 (broad), 3.2–4.0 (broad), 5.90, 6.08, 6.17, 6.37, 6.96, 7.32, 7.57 (broad), 7.87, 8.60, 9.26, 9.52, 11.0, 12.69, 13.44, and 14.10μ.

EXAMPLE 4

1,2,3,4,6,7,8,9-Octahydro-5H-4a-azonia-2a,7,9a-triazacycloocta[cd]pentalene chloride A mixture of 0.52 g of 1,4,7,10-tetraazacyclododecane, 0.32 g of tetraazacyclododecane tetrahydrochloride, 0.77 g of ethyl orthocarbonate, and 5 ml of absolute ethyl alcohol was heated with stirring on a steam bath (ca. 100°C) for 8 hours. The nmr spectrum of a small sample of the mixture indicated that the desired reaction was about 75–80% complete. The mixture was heated with stirring on a steam bath for 19 hours more. Volatile materials were evaporated under reduced pressure, and the residue was recrystallized from acetonitrile to give 0.20 g of 1,2,3,4,6,7,8,9-octahydro-5H-4a-azonia-2a,7,9a-triazacycloocta[cd]pentalene chloride (II) as needle-like crystals.

A sample of the product was dissolved in warm perdeuteroacetonitrile. The nmr spectrum of the resulting solution consisted of only two absorptions, a broad singlet (width at 1/2 height 5.5 Hz) 1.53 ppm downfield and a sharp singlet 0.83 ppm downfield from the solvent absorption. The low field absorption was assigned to the methylene protons of II, which are rapidly exchanging amongst the four different locations in structure II. This is evidence for the rapid interconversion of I, II and III.

On standing the perdeuteroacetonitrile solution deposited clear, long needles of 1,2,3,4,6,7,8,9-octahydro-5H-4a-azonia-2a,7,9a-triazacycloocta[cd]pentalene chloride. The product was a monohydrate, mp 133°–136°C, which kept its water of hydration on drying at 80°C and 0.1 mm.

Anal. Calcd. for $C_9H_{17}N_4Cl\cdot H_2O$: C, 46.05; H, 8.15; N, 23.87
Found: C, 46.04; H, 7.67; N, 24.08
46.08  7.99  24.05

As previously noted, 1,4,7,10-tetraazatetracyclo[5.5.1.0$^{4,13}$.0$^{10,13}$]tridecane (I) can be made from the product of the foregoing example (II) by treatment with one or more equivalents of sodium hydroxide. Similarly, and as also previously noted, 1,2,3,4,6,7,8,9-octahydro-5H-4a-azonia-2,7,9a-triazacycloocta[cd]pentalene chloride hydrochloride (III) can be made by treatment of the product of the foregoing example with one or more equivalents of hydrochloric acid.

1,4,7,10-Tetraazacyclododecane, the starting material in the foregoing example, can be prepared by the method of Stetter and Mayer, Chem. Ber. 94, 1410 (1961).

As illustrated in the following examples, the products of the invention are useful as sensitizers in photographic emulsion systems, and can be employed in developer systems for silver halide emulsion to reduce fog, to reduce the toe of the optical density/exposure curve, and to assist contrast without substantial loss of speed.

EXAMPLE B

To an acidified solution of gelatin containing 1.5 moles of potassium chloride there was rapidly added 1.5 moles of silver nitrate in aqueous solution. There was then added 0.6 moles of aqueous potassium bromide solution and the mixture allowed to ripen for ten minutes, after which there was added 0.9 moles of aqueous potassium bromide solution and the mixture allowed to ripen for 10 minutes, all at 160°F. The resulting emulsion was cooled, coagulated, washed, and redispersed in the manner disclosed in Moede, U.S. Pat. No. 2,772,162 issued Nov. 27, 1956. Two emulsions were made in this manner; number one a control as described, and number two a test containing 0.3 g of 1,2,3,4,6,7,8,9-octahydro-5H-4a-azonia-2a,7,9a-triazacycloocta[cd]pentalene chloride hydrochloride (III) dissolved in the acidified solution of gelatin before the silver nitrate solution was added.

The acidified gel solution contains 0.0768 moles of HCl, which is sufficient to produce a pH $\cong$ 2 with 50 g of gelatin plus 1.5 moles of KCl dissolved in 2564 ml of solution. The 0.3 g of the test compound is equal to 0.0012 moles based on formula III. The HCl present would have been adequate to produce the chloride hydrochloride in solution, and still leave sufficient HCl to produce an acid "make", if the conjugate base, 1,4,7,10-tetraazatetracyclo[5.5.1.0$^{4,13}$.0$^{10,13}$]tridecane (I), or the chloride of its monoprotonated conjugate acid, II, had been used as the test compound. Emulsions number one and number two were treated in two different ways:

(1) Negative Acting Primitive Emulsion

To the emulsion containing silver halide equivalent to 1.5 moles of silver nitrate there was added 124 g of gelatin and the temperature raised to 130°F. The pH was adjusted to 8 with borax and the emulsion digested for 40 minutes at 130°F. The pH was then adjusted to 5.5, coating aids including a gelatin hardener added, and the emulsion coated on a 4 mil polyester film support, and dried in the conventional manner.

A strip of each coated emulsion was exposed through a $\sqrt{2}$ wedge by means of a quartz-iodine lamp that provided an exposure of 514,000 meter-candle-seconds. It was then developed for 1.5 minutes at 80°F in a commercial hydroquinone-formaldehyde litho developer, and fixed, washed, and dried in a conventional manner. Densities were then read in a conventional densitometer. The results are shown in the following table.

RESPONSE OF NEGATIVE ACTING PRIMITIVE EMULSION

| Make Variation | D-Min | D-Max |
|---|---|---|
| No. 1 Control | .03 | .08 |
| No. 2 | .05 | .35 |

The greater response of emulsion number two shows that III acts as a sensitizer.

(2) Direct Positive Emulsion

To the emulsion containing silver halide equivalent to 1.5 moles of silver nitrate there was added 124 g of gelatin and the temperature raised to 130°F. A chemical fogging agent was added as described in Bigelow, U.S. Pat. No. 3,637,392 issued Jan. 25, 1972, the pH adjusted to 8 with borax and the mixture digested for 40 minutes at 130°F. The pH was then adjusted to 5.5, coating aids including a gelatin hardener added, and the emulsion coated on a 4 mil polyester film support, dried in a conventional manner and tested by the procedure described in part (1). The results are shown in the following table.

RESPONSE OF DIRECT POSITIVE EMULSION

| Make Variation | D-Min | D-Max | Speed (D=1.0) |
|---|---|---|---|
| No. 1 Control | .03 | 2.15 | 100 |
| No. 2 | .06 | 3.89 | 24 |

The higher D-max and accompanying lower speed of make variation number two which is obtained with the same amount of chemical fogging agent as the control make number one is indicative of greater sensitization, i.e., easier change obtained in make number two containing III.

EXAMPLE C

A commercial lithofilm was exposed for four seconds through a $\sqrt{2}$ step wedge and a 100 line square dot gray screen to produce test films. Test films were developed for 2 minutes at 80°F in a commercial litho developer as a control, and in the same developer to which 100 mg/liter of 1,2,3,4,6,7,8,9-octahydro-5H-4a-azonia-2,7,9a-triazacycloocta[cd]pentalene chloride hydrochloride had been added. The base fog of the control had an optical density of 0.08 compared with 0.04 when the additive was used. Table I shows the results obtained for the differing steps.

TABLE I

| Step No. | Optical Density | |
|---|---|---|
| | Control | With Additive |
| 2 | 0.03 | 0.00 |
| 3 | 0.50 | 0.05 |
| 4 | 1.24 | 0.94 |
| 5 | 2.03 | 1.99 |
| 6 | 2.89 | 2.83 |
| 7 | 3.98 | 3.95 |
| 8 | 5.08 | 5.29 |
| 9 | 5.65 | 5.59 |
| 10 | 5.64 | 5.68 |

From the data of Table I the speed of the developer with additive was 98.5 compared with a value of 100 for the control. Contrast was 6.43 compared with 5.34 for the control. The data show that the toe of the optical density/exposure curve was substantially diminished by the presence of the additive.

We claim:

1. A compound having the formula

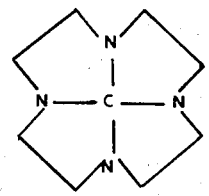

and salts thereof with an acid selected from the group consisting of hydrochloric, sulfuric, nitric, acetic, tartaric and lactic.

2. A compound of claim 1 in the form of a salt with one equivalent of said acid.

3. The compound of claim 2 wherein said acid is hydrochloric acid.

4. A compound of claim 1 in the form of a salt with two equivalents of said acid.

5. The compound of claim 4 wherein said acid is hydrochloric acid.

* * * * *